(12) United States Patent
Shallenberger

(10) Patent No.: US 7,666,137 B2
(45) Date of Patent: Feb. 23, 2010

(54) METHOD FOR ANALYZING MITOCHONDRIAL FUNCTION

(76) Inventor: Frank Shallenberger, 1231 Country Club Dr., Carson City, NV (US) 89703

( * ) Notice: Subject to any disclaimer, the term of this patent is extended or adjusted under 35 U.S.C. 154(b) by 50 days.

(21) Appl. No.: 12/081,072

(22) Filed: Apr. 10, 2008

(65) Prior Publication Data

US 2009/0259111 A1 Oct. 15, 2009

(51) Int. Cl.
*A61B 5/00* (2006.01)
(52) U.S. Cl. .................. 600/300; 600/529; 600/532
(58) Field of Classification Search .................. None
See application file for complete search history.

(56) References Cited

U.S. PATENT DOCUMENTS

| | | | |
|---|---|---|---|
| 5,117,674 | A | 6/1992 | Howard |
| 5,639,471 | A | 6/1997 | Chait |
| 5,660,176 | A | 8/1997 | Iliff |
| 5,705,735 | A | 1/1998 | Acorn |
| 5,810,722 | A | 9/1998 | Heikkila |
| 5,860,918 | A | 1/1999 | Schradi |
| 5,954,640 | A | 9/1999 | Szabo |
| 5,989,188 | A | 11/1999 | Birkhoelzer |
| 6,074,345 | A | 6/2000 | Van Oostrom |
| 6,126,595 | A | 10/2000 | Amano |
| 6,159,131 | A | 12/2000 | Pfeffer |
| 6,270,457 | B1 | 8/2001 | Bardy |
| 6,280,380 | B1 | 8/2001 | Bardy |
| 6,387,053 | B1 | 5/2002 | Pessenhofer |
| 6,478,736 | B1 | 11/2002 | Mault |
| 6,500,117 | B1 | 12/2002 | Hancock |
| 6,510,430 | B1 | 1/2003 | Oberwager |
| 6,547,729 | B1 | 4/2003 | Abbo |
| 6,554,776 | B1 | 4/2003 | Snow |
| 6,569,624 | B1 | 5/2003 | Weindruch et al. |
| 6,605,038 | B1 | 8/2003 | Teller |
| 6,620,078 | B2 | 9/2003 | Pfeffer |
| 2001/0053883 | A1 | 12/2001 | Yoshimura |
| 2002/0151815 | A1 | 10/2002 | Kawanishi |
| 2002/0193702 | A1 | 12/2002 | Yamazaki |
| 2003/0023145 | A1 | 1/2003 | Lee |
| 2003/0060690 | A1 | 3/2003 | Jellife |
| 2003/0125611 | A1 | 7/2003 | Bardy |
| 2003/0130567 | A1 | 7/2003 | Mault |

OTHER PUBLICATIONS

Perry, et al. 1998.. Prospective study of serum gamma-glutamyltransferase and risk of NIDDM. Diabetes Care 21 :732-737.
Li, J., et al., Influence of Body Fat Distribution on Oxygen Uptake and Pulmonary Performance in Morbidly Obese Females During Exercise, Respirology, 6(1), 9-13, Mar. 2.
Moon, Jon K, et al., Combined Heart Rate and Activity Improve Estimates of Oxygen Comsumption and Carbon Dioxide Production Rates, Journal of Applied Physiology, 81(4), 1754-6.
Rumpler, W.V., et al., Repeatability of 24-H Energy Expenditure Measurements in Humans by Indirect Calorimetry, American Journal of Clinical Nutrition, 51(2), 147-152.
Schoeller, Dale A., Balancing Energy Expenditure and Body Weight, American Journal of Clinical Nutrition, 68(4), 956S-961S, Oct. 1998.
Bursting With Energy, http://www.burstingwithenergy.com.
Mount Diablo Integrated Wellness, http://www.wcwellness.com/bio.html.
Shallenberger, Bursting With Energy, inMED Publishing, 2002, USA, ISBN 0-9717710-0-6, pp. 32-49.

*Primary Examiner*—Robert L Nasser
(74) *Attorney, Agent, or Firm*—Andreas Baltatzis; Kramer & Amado, P.C.

(57) ABSTRACT

A method for analyzing the mitochondrial function of a subject involves: conducting a first test wherein the average oxygen consumption of the subject during exercise is measured while the subject is breathing air having a first oxygen concentration, preferably room air having a concentration of 20-21% by weight; conducting a second test wherein the average oxygen consumption of the subject during exercise is measured while the subject is breathing air having a second oxygen concentration, preferably air having an oxygen concentration of 30-33% by weight; measuring first and second energy quotients obtained from the first and second tests, respectively; and then using the energy quotients to calculate the subject's Mitochondrial Factor. The Mitochondrial Factor is directly proportional to the subject's mitochondrial efficiency and function. If conducted periodically, the method can be used to determine whether the subject's mitochondrial efficiency is increasing or decreasing over time. The rate of increase or decrease will indicate the subject's risk of developing one or more age-related diseases.

9 Claims, No Drawings

METHOD FOR ANALYZING MITOCHONDRIAL FUNCTION

BACKGROUND OF THE INVENTION

This invention relates generally to a method for analyzing a subject's mitochondrial function.

In U.S. Pat. No. 7,273,453, which is hereby incorporated by reference in its entirety, the present inventor described a number of methods for analyzing the biological age of a subject. The methods analyzed the biological age as it related to a number of factors indicating levels of health, energy production and metabolism.

It has been found that as a subject ages, his or her mitochondrial efficiency decreases, leading to a risk of developing one or more age-related diseases. Mitochondria are intracellular inclusions that convert oxygen into energy and water. Each cell has from hundreds to thousands of mitochondria. Mitochondrial efficiency in converting oxygen into energy and water, i.e., the amount of energy produced per molecule of oxygen consumed, is important in the aging process. In addition, the risk of acquiring an age-related disease is contingent at least in part on the efficiency of this conversion. Mitochondrial efficiency in making the conversion is known to gradually and continually decrease as one ages beyond thirty-forty years old.

One reason for decreased mitochondrial efficiency during aging is that less oxygen is being delivered to the mitochondria. This may happen because of decreased circulation, decreased capacity for blood to deliver oxygen (i.e., anemia), or decreased absorption of oxygen through the lungs. Another reason for decreased mitochondrial efficiency during aging is the decreased functioning of the mitochondria themselves.

It is desirable to provide an accurate method for analyzing a subject's mitochondrial function.

SUMMARY OF THE INVENTION

In light of the present need for an accurate method for analyzing the mitochondrial function of an individual, a brief summary of the present invention is presented. Some simplifications and omissions may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention is directed to a method for analyzing a subject's mitochondrial function, involving:

1) obtaining age, body fat percentage, weight and sex information from the subject;
2) calculating the subject's predicted maximum oxygen consumption at a specified respiratory exchange ratio, the predicted maximum oxygen consumption being based on the subject's sex, body fat percentage, weight and age in years, wherein the age in years of a subject over a predetermined age is a default age, and the age in years of a subject under a predetermined age is the subject's actual age;
3) conducting a first test while the subject is breathing air having a first concentration of oxygen (preferably room or ambient air, which generally has an oxygen content of about 20-21% by weight), involving:
   a) measuring the subject's average oxygen consumption at the specified respiratory exchange ratio when the subject is exercising; and
   b) calculating a first energy quotient for the subject by dividing the subject's average oxygen consumption measured in step 3a) by the subject's predicted maximum oxygen consumption to obtain a first energy quotient for the subject;
4) conducting a second test while the subject is breathing air having a second concentration of oxygen (preferably 30-33% by weight), the first and second concentrations of oxygen being such that the amount of oxygen delivered to the subject's mitochondria in the second test is 50% higher than the amount of oxygen delivered to the subject's mitochondria in the first test, the second test involving:
   a) measuring the subject's average oxygen consumption at the specified respiratory exchange ratio when the subject is exercising;
   b) calculating a second energy quotient for the subject by dividing the subject's average oxygen consumption measured in step 4a) by the subject's predicted maximum oxygen consumption; and
5) calculating a Mitochondrial Factor for the subject using the equation:

$$\text{Mitochondrial Factor} = \frac{(EQ2 - EQ1) \times 200}{EQ1}$$

EQ1 being the first energy quotient and EQ2 being the second energy quotient, wherein the Mitochondrial Factor is directly proportional to the subject's mitochondrial efficiency and function.

The method of this invention preferably further includes determining the subject's Mitochondrial Factor periodically so as to determine whether the subject's mitochondrial efficiency is increasing or decreasing over time and the rate at which the mitochondrial efficiency is increasing or decreasing. The rate of increase or decrease will indicate the subject's risk of developing one or more age-related diseases. If a pattern of rate increase is seen, interventions can be taken to stop and even reverse the development of an age-related disease.

DETAILED DESCRIPTION OF THE PREFERRED EMBODIMENTS OF THE INVENTION

The present invention describes a method for analyzing a subject's mitochondrial function, specifically the subject's mitochondrial efficiency.

In the method of this invention, certain physical characteristics of the subject are first measured. These physical measurements are the subject's age, body fat percentage, weight and sex information. These measurements are then used to calculate the subject's predicted maximum oxygen consumption at a specified respiratory exchange ratio, e.g., 0.85 or 1.00.

Specifically, the predicted maximum oxygen consumption for a person based on the age, sex, weight, and body fat percentage of the patient is determined as follows: predicted maximum oxygen consumption for a male=[weight (in kilograms)×(1−(body fat percentage/100))/0.82]×(50.72−(0.372×age)). Predicted maximum oxygen consumption for a female=([weight (in kilograms)×(1−(body fat percentage/100))/0.78]+43)×(22.78−(0.17×age)).

Accurately analyzing the mitochondrial function of a subject requires taking the equations for calculating predicted maximum oxygen consumption and adjusting them for age.

In a preferred embodiment of the invention, when calculating predicted maximum oxygen consumption for a subject whose actual age in years is over a predetermined age, a default age is used instead. In a more preferred embodiment of the invention, the predetermined age is 35-60. In a further-preferred embodiment, the predetermined age is forty (40). The predetermined age and default age may be different. In a further preferred embodiment of the invention, the predetermined age is equal to the default age. In another preferred embodiment, when calculating predicted maximum oxygen consumption for a subject whose actual age is under forty (40), the actual age of the subject is used. A further preferred embodiment may be illustrated by the following examples: For a subject with actual age greater than the predetermined age: Subject's actual age is 50, greater than the predetermined age of 40, a default age of 40 is used to calculate the subject's predicted maximum oxygen consumption. For a subject with actual age less than the predetermined age: Subject's actual age is 35, lower than the predetermined age of 40, the subject's actual age of 35 is used to calculate the subject's predicted maximum oxygen consumption.

In the method of this invention, after the subject's predicted maximum oxygen consumption at a specified respiratory exchange ratio is measured, the subject's actual oxygen consumption is measured. The first test measures average oxygen consumption while the subject is exercising.

In the first test, the subject is breathing air having a first concentration of oxygen, preferably ambient or room air, which has an oxygen concentration of about 20-21%, more preferably about 21%, by weight.

The subject's average oxygen consumption measured in the first test is divided by the subject's predicted maximum oxygen consumption to obtain a first energy quotient, EQ1, for the subject.

The second test of the method is preferably carried out as soon as the subject's heart rate has returned to a normal resting reading after the first test. In the second test, the subject's average oxygen consumption is measured while the subject is exercising and breathing air having a second concentration of oxygen. The first concentration of oxygen used in the first test and the second concentration of oxygen used in the second test are such that the amount of oxygen delivered to the subject's mitochondria in the second test is 50% higher than the amount of oxygen delivered to the subject's mitochondria in the first test. When the first test uses room air, i.e., the first oxygen concentration is about 20-21% by weight, the air used in the second test preferably contains about 30-33%, more preferably about 31.5-32.5%, by weight of oxygen. The second test is typically carried out with special equipment added to the mouthpiece that allows the subject to breath air having an oxygen concentration of about 30-33% by weight.

The subject's respiratory exchange ratio is the same in both the first and second tests and in the calculation of the subject's predicted maximum oxygen consumption value. Preferably, the respiratory exchange ratio is about 1.00.

The subject's average oxygen consumption measured in the second test is divided by the subject's predicted maximum oxygen consumption to obtain a second energy quotient, EQ2, for the subject.

The Mitochondrial Factor is then calculated from the first and second energy quotients according to the following equation:

$$\text{Mitochondrial Factor} = \frac{(EQ2 - EQ1) \times 200}{EQ1}.$$

The Mitochondrial Factor is directly proportional to the subject's mitochondrial efficiency. A Mitochondrial Factor of 100 or higher implies that the subject's total mitochondrial function is optimal. A Mitochondrial Factor of 0.0 indicates significant impairment of mitochondrial function.

As discussed above, the first test in the mitochondrial-function-based method of this invention calculates a first energy quotient based on average oxygen consumption during exercise, while the subject is breathing air having a particular concentration of oxygen. The first energy quotient will measure total mitochondrial efficiency, but when the energy quotient of the subject is low, measuring it alone will not delineate whether or not the decrease is due to poor oxygen delivery or to an actual dysfunction of the mitochondria. A second energy quotient, measured at a different oxygen concentration in the air breathed by the subject, is useful in this regard.

The Mitochondrial Factor demonstrates the relationship between the amount of oxygen delivered to the mitochondria and the energy output of the mitochondria. In healthy, young subjects (those with optimal mitochondrial function), when the oxygen delivered to the mitochondria is increased by 50%, there is a corresponding 50% increase in the energy quotient. In other words, when the amount of oxygen delivered to healthy mitochondria is increased by 50%, the second energy quotient, EQ2, will be 50% higher than the first energy quotient, EQ1, and the Mitochondrial Factor will equal 100. This is because as the amount of oxygen delivered to healthy mitochondria is increased by 50%, the total mitochondrial output will correspondingly increase by the same amount. This indicates fully efficient mitochondria. The more oxygen delivered to healthy mitochondria, the more energy such mitochondria can produce. On the other hand, in subjects having decreased mitochondrial efficiency, simply increasing the amount of oxygen delivered to the mitochondria will not result in a corresponding increase in energy production. A Mitochondrial Factor of 0.0 indicates that there was no corresponding increase in energy output when the amount of oxygen delivered to the mitochondria was increased 50%. This indicates significant impairment of the efficiency at which the mitochondria are functioning.

The present invention further includes a method for determining whether a subject's mitochondrial efficiency is increasing or decreasing over time, involving repeating periodically, preferably annually, the above-described method. An increase or decrease of a subject's Mitochondrial Factor over time indicates, respectively, an increase or decrease of the subject's mitochondrial efficiency over time. From this, the rate at which the mitochondrial efficiency is increasing or decreasing can be determined, which in turn will indicate the subject's risk of developing one or more age-related diseases. If a pattern of rate increase is seen, interventions can be taken to stop and even reverse the development of an age-related disease.

The subject's average oxygen consumption at a specified respiratory exchange ratio when the subject is exercising and when he or she is at rest can be determined using breath-by-breath measurements, as described in detail in U.S. Pat. No. 7,272,453, which was previously incorporated by reference herein in its entirety. Breath-by-breath measurements are typically taken using a specialized device such as a pulmonary gas exchange analyzer.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A method for analyzing the mitochondrial function of a subject, comprising:
   1) obtaining age, body fat percentage, weight and sex information from the subject;
   2) calculating the subject's predicted maximum oxygen consumption at a specified respiratory exchange ratio using an analyzer, the predicted maximum oxygen consumption being based on the subject's sex, body fat percentage, weight and age in years, wherein the age in years of a subject over a predetermined age is a default age, and the age in years of a subject under a predetermined age is the subject's actual age;
   3) coupling the subject to a pulmonary breath analyzer via a mouthpiece, and conducting a first test while the subject is breathing air having a first concentration of oxygen, the first test comprising:
      a) measuring the subject's average oxygen consumption at the specified respiratory exchange ratio when the subject is exercising; and
      b) calculating a first energy quotient for the subject by dividing the subject's average oxygen consumption measured in step 3a) by the subject's predicted maximum oxygen consumption to obtain a first energy quotient for the subject;
   4) conducting a second test while the subject is breathing air having a second concentration of oxygen administered by use of the mouthpiece, the first and second concentrations of oxygen being such that the amount of oxygen delivered to the subject's mitochondria in the second test is 50% higher than the amount of oxygen delivered to the subject's mitochondria in the first test, the second test comprising:
      a) measuring the subject's average oxygen consumption at the specified respiratory exchange ratio when the subject is exercising; and
      b) calculating a second energy quotient for the subject by dividing the subject's average oxygen consumption measured in step 4a) by the subject's predicted maximum oxygen consumption; and
   5) calculating a Mitochondrial Factor for the subject using the equation:

$$\text{Mitochondrial Factor} = \frac{(EQ2 - EQ1) \times 200}{EQ1}$$

EQ1 being the first energy quotient and EQ2 being the second energy quotient, wherein the Mitochondrial Factor is directly proportional to the subject's mitochondrial efficiency.

2. The method of claim 1, wherein the first oxygen concentration is about 20-21% by weight, and the second oxygen concentration is about 30-33% by weight.

3. The method of claim 1, wherein the first oxygen concentration is about 21% by weight, and the second oxygen concentration is about 31.5-32.5% by weight.

4. The method of claim 1, wherein the specified respiratory exchange ratio is about 1.00.

5. A method for determining whether a subject's mitochondrial efficiency is increasing or decreasing over time, comprising repeating the method of claim 1 on a periodic basis, wherein an increase or decrease of a subject's Mitochondrial Factor over time indicates, respectively, an increase or decrease of the subject's mitochondrial efficiency over time.

6. A method according to claim 5, wherein the method of claim 1 is repeated annually.

7. The method of claim 5, wherein the first oxygen concentration is about 20-21% by weight, and the second oxygen concentration is about 30-33% by weight.

8. The method of claim 5, wherein the first oxygen concentration is about 21% by weight, and the second oxygen concentration is about 31.5-32.5% by weight.

9. The method of claim 5, wherein the specified respiratory exchange ratio is about 1.00.

* * * * *